United States Patent [19]

Okano

[11] Patent Number: 4,533,253
[45] Date of Patent: Aug. 6, 1985

[54] DEVICE FOR MEASURING DENSITY OF PHOTOGRAPHIC TRANSPARENCY

[75] Inventor: Takeshi Okano, Nishinomiya, Japan

[73] Assignee: Konan Camera Research Institute, Nishinomiya, Japan

[21] Appl. No.: 415,447

[22] Filed: Sep. 7, 1982

[30] Foreign Application Priority Data

Sep. 16, 1981 [JP] Japan ................ 56-146927

[51] Int. Cl.³ ............................................ G01N 21/59
[52] U.S. Cl. .................... 356/443; 356/365; 356/404; 356/407
[58] Field of Search ............... 356/404, 405, 406, 407, 356/365, 443, 444

[56] References Cited

U.S. PATENT DOCUMENTS 4,198,123  4/1980  Kremen ..................... 356/317

Primary Examiner—F. L. Evans
Attorney, Agent, or Firm—Eugene E. Geoffrey, Jr.

[57] ABSTRACT

A device for measuring density of photographic transparencies, such as recorded photographic film, which is generally used in a color scanner system in which a photographic film carrying a colored image is scanned in X and Y directions with a light beam, so-called "flying spot", and the transmitted beam is separated into a plurality of component color beams which are then converted into electric signals indicative of densities of the respective component colors, which are then adequately adjusted in magnitude and utilized for preparation of multi-color printing blocks, the device having means for correcting density errors relating to polarization characteristics of the material of the film.

4 Claims, 1 Drawing Figure

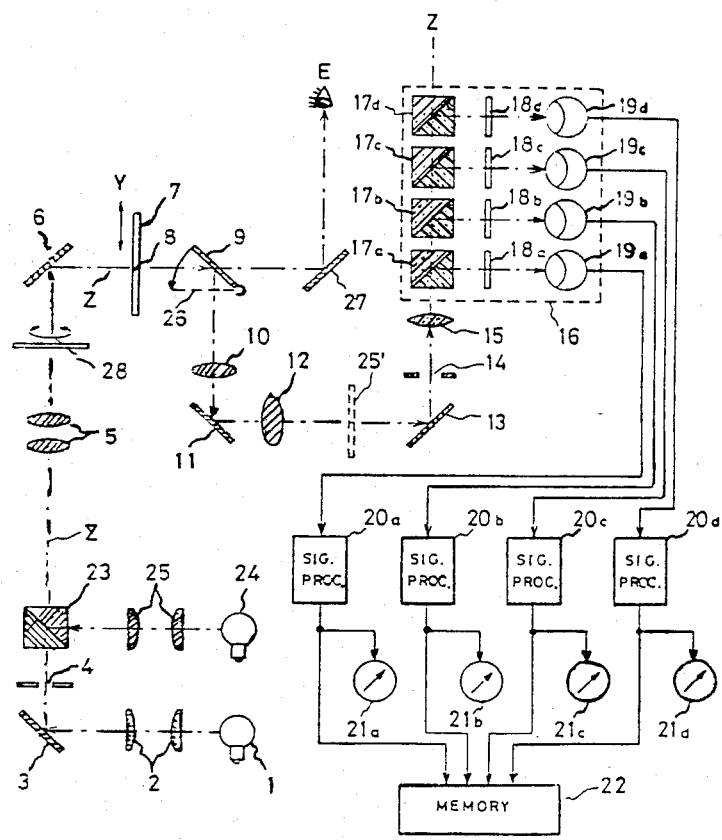

DEVICE FOR MEASURING DENSITY OF PHOTOGRAPHIC TRANSPARENCY

This invention relates generally to a color scanner system, and especially to a device used in this system for measuring density of a colored image recorded on a photographic film for the purpose of determining color correcting and/or printing conditions.

The color scanner is a device used for preparation of color printing blocks from a color photographic transparency and is described, for example, in the article of Yoshio Ono entitled "Overview of Color Scanners", Jour. Jap. Soc. Image Electronics, Volume 9, No. 2 (1980) pp. 93–101. In the color scanner, a color photographic transparency is scanned with a light beam, so-called "flying spot", and the transmitted beam is separated into primary color beams which are then converted into corresponding electric color signals. In order to compensate for the inherent difference in density between photography and printing, these color signals are then subjected to correction processings, such as logarithmic compression, density correction and contrast control, based upon the overall density distribution of the photograph.

As the color signals are indicative of densities of the respective colors, the color densities of the transparency can be known by indicating the levels of color signals on suitable meters after proper processing such as amplification. It has been found that the meters sometime indicate negative densities when the measured region of the transparency is nearly clear and transparent, that is, at nearly zero density level. This means that insertion of a clear transparent film between a light source and a photoelectric element results in an increase in the amount of incident light, instead of a decrease.

While the material of photographic film generally consists of cellulose acetate polymer, polyester may be used in a large-sized photographic film for preventing its deformation due to heat and moisture. It has been found that the above mentioned phenomenon appears on photographic film made of polyester base material.

Furthermore, in the device for measuring density of a photographic transparency, some optical components, such as an interference half-mirror having a polarizing effect, are disposed between the light source and the photoelectric element for the purpose of satisfying various utilization conditions and design requirements of the device. If the planes of polarization of such polarizing optical components are crossed, the amount of light incident upon the photoelectric element will be reduced. In this case, however, if an optical medium having such function as rotating the plane of plarization or scattering the polarized light into normal light should be disposed between the two polarizing components, the reduced amount of incident light would be restored or increased again.

Though not yet studied sufficiently, it is supposed that the above mentioned polyester film has a feature relating to polarization as described above. This invention intends to provide the device for measuring density of photographic transparency with novel and improved means for restoring reduction of light intensity due to polarizing effects of some optical components on the basis of the above consideration.

According to the invention, a device is provided for measuring density of a photographic transparency, which includes a light source for illuminating the transparency, a photoelectric element for converting the incident light into an electric signal, and at least two optical components having a polarizing effect. As a feature of this invention, an optical medium for restoring polarized light into normal light is disposed between the two optical components, so that it is rotated about the axis of polarization to minimize the reduction of intensity.

Now, the description will be made in detail hereinunder with reference to the accompanying drawing.

The single drawing shows an embodiment of the device of this invention.

In the drawing, light from a measuring light source 1 is focused through condenser lens 2, reflecting mirror 3 and pin hole 4 and then passes focusing lens 5 and reflecting mirror 6 to form a fine illuminating spot 8 on a photographic transparency 7. The light transmitted through the transparency 7 at the spot 8 passes a movable reflecting mirror 9, lens 10, reflecting mirror 11, lens 12, reflecting mirror 13, iris 14 and lens 15 and enters a multi-color receiver 16. In the multi-color receiver 16, the incoming light is separated into four beams by four half mirrors 17a, 17b, 17c and 17d and the separated beams pass four color filters 18a, 18b, 18c and 18d and enter four photoelectric elements 19a, 19b, 19c and 19d, respectively.

Electric output signals of the photoelectric elements 19a, 19b, 19c and 19d, which are indicative of densities of the respective component colors in the photographic transparency 7, are subjected to amplification and other proper conventional processings in signal processing circuits 20a, 20b, 20c and 20d, respectively, and applied to meters 21a, 21b, 21c and 21d for indication and to memory 22 for storage.

When, in this arrangement, the transparency 7 is moved reciprocatingly at high speed in the X direction (direction normal to the paper plane) orthogonal to optical axis Z and, at the same time, at low speed in the Y direction (as shown by arrow) orthogonal to both X and Z directions, the transparency 7 is scanned by the spot 8 at high speed in the X direction and at low speed in the Y direction. Thus, the memory 22 stores densities of the respective component colors of the transparency 7 along the scan lines for future utilization.

When the X-Y scan of the transparency 7 is interrupted to illuminate a specific point of the image, the device can be used for measuring color densities of this point. In this case, it is convenient for aiming at the specific point if some area of the image surrounding this aimed point can be observed. For this purpose, a half mirror 23 is inserted in the light path along the optical axis Z and another light is introduced therein from an observing light source 24 through condenser lens 25. When the movable mirror 9 is rotated to another position as shown by dashed line 26, the focused spot 8 on the photographic transparency 7 can be observed by the eye E through reflecting mirror 27 together with the surrounding area of the image on the transparency 7 which is illuminated by the light source 24.

The above mentioned problem in density measurement due to polarization has come from the fact that the half-mirrors 17a through 17d and 23 have some polarizing feature and, moreover, always exist in the optical system for measurement. While the half-mirrors are shown to be of the double-prism type, it has been known that the polarizing feature can be reduced substantially by using those of the metal deposition type. However, the percent transmission is reduced by as much as 30 percent per transmission and, accordingly, a large reduction is caused in the illumination of the respective photoelectric elements 19a through 19d. In fact, the amount of light incident upon the last photoelectric element 19d is reduced to about 1/120 of the initial value.

As well known, in the half-mirror, the reflected light is polarized in the direction normal to the plane of incidence (plane including the incident light and the reflected and transmitted light) and the transmitted light is polarized in the direction parallel to that plane. Accordingly, if the planes of incidence of the half-mirrors 17a through 17d are parallel to the plane of incidence of the half-mirror 23, the amount of illumination of the photoelectric element 19a is unchanged, while those of the other elements 19b, 19c and 19d are reduced. Contrarily, if the plane of incidence of the half-mirrors 17a through 17d is perpendicular to that of the half-mirror 23, the amount of light incident upon the element 19a is reduced, while those of the other elements 19b, 19c and 19d are left unchanged. The signal processing circuits 20a, 20b, 20c and 20d are previously adjusted so that, when the photograhic transparency 7 is removed to maximize the amount of light incident upon the photoelectric elements 19a through 19d, their output levels corresponding to the zero density are indicated as zeros on the meters 21a through 21d, respectively. Accordingly, with insertion of a photographic film having such particular feature relating to polarization as aforementioned, the amount of light incident upon the elements 19a through 19d may be increased in clear and transparent areas of the film to render the indications of the meters 21a through 21d negative.

According to this invention, a polyester film 28 having a similar feature to the transparency 7 of restoring polarized light into natural light is inserted between the half-mirror 23 and the half-mirrors 17a through 17d. With the transparency 7 removed, the film 28 is rotated about the axis Z as shown by arrow and the angle of rotation is fixed at the position where the maximum amounts of light are incident upon the photoelectric elements 19a through 19d. Then, the meters 21a through 21d are calibrated so as to indicate zeros, respectively. Thereafter, the transparency 7 is inserted to effect density measurement. Then, the light from the measuring light source 1 is once polarized by the half-mirror 23 but restored to natural light by the polyester film 28, thereby minimizing variation in illumination of the elements 19a through 19d due to polarization relating feature of the transparency 7.

It should be noted that the above description has been made for explanation purposes only and various modifications and changes can be made within the scope of this invention by those skilled in the art. For example, the polyester film 28 may be disposed beyond the transparency 7 as shown by dashed line 25'. Moreover, the polyester film may be substituted with other suitable material or optical component having the feature of restoring polarized light to natural light.

What is claimed is:

1. A device for measuring density of photographic transparency, comprising a light source, a photoelectric element, at least two optical components having a polarizing feature and being disposed on a light path between said light source and photoelectric element, and a location on said light path between said optical components where a photographic transparency to be measured is to be located, optical means for restoring polarized light to natural light, said means being disposed rotatably in said light path between said optical components, and the angle of rotation of said optical means being adjusted so that the amount of incident light on said photoelectric element is maximized when said photographic transparency is removed from said location.

2. The device, according to claim 1, wherein said optical means includes a polyester film.

3. A method for measuring density of a photographic transparency, using a device comprising a light source, a photoelectric element, at least two optical components having a polarizing feature and being disposed on a light path between said light source and photoelectric element, and a location on said light path between said optical components where a photographic transparency to be measured is to be located, said method comprising the steps of disposing optical means for restoring polarized light to natural light between said optical components on said light path and rotating said means about said light path to adjust the amount of incident light on said photoelectric element to the maximum before measurement with said photographic transparency removed from said location.

4. The method, according to claim 3, wherein said optical means includes a polyester film.

* * * * *